(12) United States Patent
Takahashi et al.

(10) Patent No.: US 8,153,109 B2
(45) Date of Patent: Apr. 10, 2012

(54) ALKYLENE CARBONATE DILUTION, ALKYLENE CARBONATE FOR PREPARING THE DILUTION, AND AQUEOUS REDUCING CHEMICAL AGENT

(75) Inventors: Masanobu Takahashi, Tokyo (JP); Masumi Koike, Tokyo (JP); Hirotomi Tamura, Tokyo (JP)

(73) Assignees: San-Ei Kagaku Co., Ltd., Tokyo (JP); Showa Denko K.K., Tokyo (JP)

( * ) Notice: Subject to any disclaimer, the term of this patent is extended or adjusted under 35 U.S.C. 154(b) by 1176 days.

(21) Appl. No.: 11/943,072

(22) Filed: Nov. 20, 2007

(65) Prior Publication Data

US 2008/0118455 A1    May 22, 2008

(30) Foreign Application Priority Data

Nov. 21, 2006  (JP) ................................ 2006-341927
Mar. 12, 2007  (JP) ................................ 2007-102196

(51) Int. Cl.
*A61Q 5/04*          (2006.01)
(52) U.S. Cl. ..................................... 424/70.5; 424/70.2

(58) Field of Classification Search .................. None
See application file for complete search history.

(56) References Cited

U.S. PATENT DOCUMENTS 3,966,903 A *  6/1976 Torii et al. ................. 424/70.4
2008/0085251 A1*  4/2008 Shibuya et al. ............. 424/70.5

FOREIGN PATENT DOCUMENTS

JP    2006-199692    8/2006
JP    2006-265187    10/2006

* cited by examiner

*Primary Examiner* — Jyothsna Venkat
(74) *Attorney, Agent, or Firm* — Young & Thompson

(57) ABSTRACT

An object of the invention is to provide an aqueous solution of a No. 1 permanent waving agent through reconstitution upon use in a simple manner, which solution contains a cyclic mercapto compound as a reducing agent and realizes excellent characteristics such as high waving effect and good appearance of waved hair. The invention provides an alkylene carbonate dilution containing a cyclic mercapto compound in an amount of 7 to 80 wt. %; an alkylene carbonate for use in preparation of the alkylene carbonate dilution; and an aqueous reducing chemical agent which is prepared from the alkylene carbonate dilution and an aqueous base material.

5 Claims, No Drawings

ALKYLENE CARBONATE DILUTION, ALKYLENE CARBONATE FOR PREPARING THE DILUTION, AND AQUEOUS REDUCING CHEMICAL AGENT

The entire disclosure of Japanese Patent Applications Nos. 2006-341927 filed Nov. 21, 2006 and 2007-102196 filed Mar. 12, 2007 is expressly incorporated by reference herein.

BACKGROUND OF THE INVENTION

1. Field of the Invention

The present invention relates to a diluted solution formed by means of alkylene carbonate (hereinafter may be referred to as an alkylene carbonate dilution) which is useful for preparing an aqueous reducing chemical agent (e.g., a No. 1 permanent waving agent); to an alkylene carbonate useful for preparing the alkylene carbonate dilution; and to an aqueous reducing chemical agent.

2. Background Art

Generally, a permanent waving agent includes an aqueous No. 1 agent, which contains a reducing substance, and a No. 2 agent, which contains an oxidizing substance.

One known reducing substance contained in such an aqueous No. 1 agent is a cyclic mercapto compound, which is disclosed in Japanese Patent Application Laid-Open (kokai) No. 2006-265187.

The patent document discloses in paragraph [0009] thereof that the stability of cyclic mercapto compounds in an aqueous solution leaves room for improvement and is to be further enhanced. The patent document also discloses that, since these specific cyclic mercapto compounds gradually decompose over time in an aqueous solution, the cyclic mercapto compound level of a water-containing chemical agent for permanent waving gradually decreases, and undesired coloring, precipitation, etc. which occur in association with decomposition impair the appearance of chemical agent products, thus problematically deteriorating the products.

One approach for solving the problem disclosed in paragraph [0011] of the same patent document is to provide an emulsified hair-treating chemical agent (No. 1 permanent waving agent) containing a cyclic mercapto compound, a surfactant, and water, whereby stability of the cyclic mercapto compound contained in the chemical agent is enhanced.

However, as disclosed in the Examples section of the patent document, percent decomposition of 2-mercapto-4-butyrolactone on test day 10 reaches, in some cases, about 30%. Therefore, such an emulsified chemical agent has a storage stability that still remains to be enhanced, and is not considered a chemical agent sufficiently suitable for mass production and long-term storage.

Under such circumstances, currently, when a No. 1 permanent waving agent containing a cyclic mercapto compound as a reducing substance is employed, the No. 1 permanent waving agent must be reconstituted upon use (just before use of a hair-treating agent).

However, since a cyclic mercapto compound has considerably low solubility in water, reconstitution of the compound upon use is difficult, which is problematic. Specifically, in order to prepare an aqueous solution of a No. 1 permanent waving agent, a cyclic mercapto compound and water must be vigorously stirred together by means of a homomixer (disclosed in paragraph [0093] of the patent document). Thus, reconstitution of the permanent waving agent upon use cannot be employed in practice.

SUMMARY OF THE INVENTION

In view of the foregoing, an object of the present invention is to provide an aqueous solution of a No. 1 permanent waving agent through reconstitution upon use in a simple manner, which solution contains a cyclic mercapto compound as a reducing agent and realizes excellent characteristics such as high waving effect and good appearance of waved hair.

In order to attain the object, the present inventors have conducted extensive studies, and have accomplished the present invention on the basis of a finding from the studies.

Accordingly, in a first mode of the present invention, there is provided an alkylene carbonate dilution comprising a cyclic mercapto compound in an amount of 7 to 80 wt. %, and an alkylene carbonate in an amount of 20 to 93 wt. %.

A second mode of the present invention is drawn to a specific embodiment of the alkylene carbonate dilution according to the first mode, wherein the cyclic mercapto compound is a 2-mercapto-lactone and/or 2-mercapto-lactam.

A third mode of the present invention is drawn to a specific embodiment of the alkylene carbonate dilution according to the second mode, wherein the 2-mercapto-lactone and/or 2-mercapto-lactam is 2-mercapto-4-butyrolactone.

A fourth mode of the present invention is drawn to a specific embodiment of the alkylene carbonate dilution according to any one of the first to third modes, wherein the alkylene carbonate is at least one selected from the group consisting of ethylene carbonate and propylene carbonate.

A fifth mode of the present invention is drawn to a specific embodiment of the alkylene carbonate dilution according to any one of the first to fourth modes, wherein the alkylene carbonate is a mixture of ethylene carbonate and propylene carbonate, and the ratio (ethylene carbonate/propylene carbonate) by weight is 90/10 to 50/50.

In a sixth mode of the present invention, there is provided an alkylene carbonate for use in preparation of an alkylene carbonate dilution containing a cyclic mercapto compound in an amount of 7 to 80 wt. %, and an alkylene carbonate in an amount of 20 to 93 wt. %.

A seventh mode of the present invention is drawn to a specific embodiment of the alkylene carbonate according to the sixth mode, wherein the cyclic mercapto compound is a 2-mercapto-lactone and/or 2-mercapto-lactam.

An eighth mode of the present invention is drawn to a specific embodiment of the alkylene carbonate according to the seventh mode, wherein the 2-mercapto-lactone and/or 2-mercapto-lactam is 2-mercapto-4-butyrolactone.

A ninth mode of the present invention is drawn to a specific embodiment of the alkylene carbonate according to any one of the sixth to eighth modes, wherein the alkylene carbonate is at least one selected from the group consisting of ethylene carbonate and propylene carbonate.

A tenth mode of the present invention is drawn to a specific embodiment of the alkylene carbonate according to any one of the sixth to ninth modes, wherein the alkylene carbonate is a mixture of ethylene carbonate and propylene carbonate, and the ratio (ethylene carbonate/propylene carbonate) by weight is 90/10 to 50/50.

In an eleventh mode of the present invention, there is provided a use of an alkylene carbonate as described in any one of the sixth to tenth modes in preparation of an alkylene carbonate dilution containing a cyclic mercapto compound in an amount of 7 to 80 wt. %, and an alkylene carbonate in an amount of 20 to 93 wt. %.

In a twelfth mode of the present invention, there is provided an aqueous reducing chemical agent comprising an alkylene carbonate dilution and an aqueous base material, wherein the alkylene carbonate dilution is contained in an amount of 3 to 35 parts by weight per 100 parts by weight of the aqueous base material, and the alkylene carbonate dilution contains a cyclic mercapto compound in an amount of 7 to 80 wt. % and an alkylene carbonate in an amount of 20 to 93 wt. %.

A thirteenth mode of the present invention is drawn to a specific embodiment of the aqueous reducing chemical agent according to the twelfth mode, which is a No. 1 permanent waving agent, a hair-straightening agent, a hair-curling agent, or a straightening permanent agent.

A fourteenth mode of the present invention is drawn to a specific embodiment of the aqueous reducing chemical agent according to the twelfth or thirteenth modes, wherein the cyclic mercapto compound is a 2-mercapto-lactone and/or 2-mercapto-lactam.

A fifteenth mode of the present invention is drawn to a specific embodiment of the aqueous reducing chemical agent according to the fourteenth mode, wherein the 2-mercapto-lactone and/or 2-mercapto-lactam is 2-mercapto-4-butyrolactone.

A sixteenth mode of the present invention is drawn to a specific embodiment of the aqueous reducing chemical agent according to any one of the twelfth to fifteenth modes, wherein the alkylene carbonate is at least one selected from the group consisting of ethylene carbonate and propylene carbonate.

A seventeenth mode of the present invention is drawn to a specific embodiment of the aqueous reducing chemical agent according to any one of the twelfth to sixteenth modes, wherein the alkylene carbonate is a mixture of ethylene carbonate and propylene carbonate, and the ratio (ethylene carbonate/propylene carbonate) by weight is 90/10 to 50/50.

According to the present invention, an aqueous solution of a No. 1 permanent waving agent can be provided through reconstitution upon use in a simple manner, which solution contains a cyclic mercapto compound as a reducing agent and realizes excellent characteristics such as high waving effect and good appearance of waved hair.

DETAILED DESCRIPTION OF PREFERRED EMBODIMENTS

The present invention will next be described in detail.

The "alkylene carbonate" according to the present invention serves as a diluent for a cyclic mercapto compound, and is exclusively employed for preparing the alkylene carbonate dilution according to the present invention.

The cyclic mercapto compound which is diluted by the diluent is preferably 2-mercapto-lactone and/or 2-mercapto-lactam (hereinafter may be referred to as "2-mercapto-lactone (lactam)"). Examples of the 2-mercapto-lactone (lactam) include the following compounds represented by formula F1:

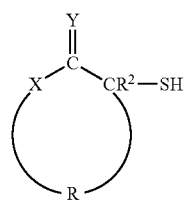

(F1)

wherein X represents any structure of —O—, —S—, —NH—, and —NR$^1$—; R$^1$ represents a C1 to C6 alkyl group; R$^2$ represents H or a C1 to C6 alkyl group; Y represents O or S; and R represents a divalent organic residue which may have a mercapto group.

Specific examples of the 2-mercapto-lactone (lactam) include 2-mercapto-4-butyrolactone (also called 2-mercapto-4-butanolide, hereinafter may be abbreviated as "MBL"), 2-mercapto-4-butyrothiolactone, 2-mercapto-4-butyrolactam, N-methyl-2-mercapto-4-butyrolactam, N-ethyl-2-mercapto-4-butyrolactam, N-(2-methoxy)ethyl-2-mercapto-4-butyrolactam, N-(2-ethoxy)ethyl-2-mercapto-4-butyrolactam, 2-mercapto-4-methyl-4-butyrolactone, 2-mercapto-4-ethyl-4-butyrolactone, 2-mercapto-5-valerolactone, 2-mercapto-5-valerolactam, N-methyl-2-mercapto-5-valerolactam, N-ethyl-2-mercapto-5-valerolactam, N-(2-methoxy)ethyl-2-mercapto-5-valerolactam, N-(2-ethoxy)ethyl-2-mercapto-5-valerolactam, and 2-mercapto-6-hexanolactam. One or more species of these compounds are employed. Among them, MBL is preferred.

In the alkylene carbonate according to the present invention, examples of the "alkylene" include C2 and C3 alkylenes. Preferably, the alkylene carbonate is ethylene carbonate and/or propylene carbonate. When the alkylene carbonate is a mixture of ethylene carbonate and propylene carbonate, the ratio (ethylene carbonate/propylene carbonate) by weight is preferably 90/10 to 50/50, particularly preferably 80/20 to 60/40. When this ratio is excessively small, a diluted solution of a cyclic mercapto compound by means of alkylene carbonate may have poor solubility in water, whereas when the ratio is excessively large, the alkylene carbonate mixture is crystallized at ambient temperature, and, in some cases, an additional heat melting process must be performed during dilution of the cyclic mercapto compound.

The alkylene carbonate dilution according to the present invention contains a cyclic mercapto compound. Specifically, the alkylene carbonate dilution is a cyclic mercapto compound diluted by means of alkylene carbonate.

In the alkylene carbonate dilution according to the present invention, the cyclic mercapto compound is any of the above-exemplified compounds. Of these, 2-mercapto-lactone (lactam) is preferred, with MBL being most preferred.

In the alkylene carbonate dilution according to the present invention, the alkylene carbonate is any of the above-exemplified species. Of these, ethylene carbonate and/or propylene carbonate is preferred.

Into the alkylene carbonate dilution according to the present invention, an additive such as a polybasic acid ester, a polyhydric alcohol, or a nonionic surfactant may be incorporated. The additive is preferably liquid.

Specific examples of the polybasic acid ester serving as the additive include di(caprylic/capric acid) propylene glycol ester, tri(caprylic/capric acid) glycerin ester, glyceryl tri(2-ethylhexanoate), triethyl citrate, acetyltributyl citrate, pentaerythritol tetra(2-ethylhexanoate), di(2-ethylhexyl) succinate, and diethyl sebacate.

Specific examples of the polyhydric alcohol serving as the additive include propylene glycol, dipropylene glycol, 1,3-butylene glycol, 3-methyl-1,3-butanediol, ethylene glycol, polyethylene glycol, propylene glycol, and polypropylene glycol.

Specific examples of the nonionic surfactant serving as the additive include POE alkyl ether, POP alkyl ether, POE/POP alkyl ether, POE/POP glycol, POE sorbitan fatty acid ester, POE castor oil, POE hydrogenated castor oil, POE sorbitol tetrafatty acid ester, alkyl polyglycoside, and N-alkyldimethylamine oxide. Preferably, the alkyl is C4 to C18. Notably, the fatty acid may be saturated or unsaturated.

Into the alkylene carbonate dilution according to the present invention, other additives may be incorporated. Examples of such additives include POP glyceryl ether, POP sorbitol, POE/POP glyceryl ether, alkyl (C12 to C15) benzoate, and organic solvents (diluents) such as lower alcohol, aromatic alcohol, and N-alkylpyrrolidone.

The alkylene carbonate dilution according to the present invention contains a cyclic mercapto compound in an amount of 7 to 80 wt. %, preferably 9 to 30 wt. %. The alkylene carbonate dilution preferably contains an alkylene carbonate in an amount of 20 to 93 wt. %, particularly preferably 70 to 91 wt. %.

When the amount of cyclic mercapto compound is excessively large (or the amount of alkylene carbonate is excessively small), in some cases, dissolution rate of the cyclic mercapto compound decreases during, for example, the below-mentioned preparation of an aqueous reducing chemical agent. In such cases, difficulty is encountered in mixing the components, and uniform liquid products may fail to be produced in a short period of time. In contrast, when the amount of cyclic mercapto compound is excessively small (or the amount of alkylene carbonate is excessively large), the waving efficiency may decrease.

The alkylene carbonate dilution according to the present invention may be prepared in a simple manner through, for example, manually shaking a mixture of a cyclic mercapto compound and alkylene carbonate under optional heating (preferably 50° C. or lower) or through uniformly mixing a cyclic mercapto compound and alkylene carbonate by means of a generally employed stirring apparatus. The uniform mixing can be performed simply and rapidly.

The thus-prepared alkylene carbonate dilution according to the present invention is generally in the form of uniform liquid; i.e., solution. However, the form of the alkylene carbonate dilution is not limited to solution, and the dilution may be in the form of viscous liquid, gel, etc.

In general, the alkylene carbonate dilution according to the present invention generally exhibits a percent decomposition of cyclic mercapto compound of 3% or lower (storage at ambient temperature over a period of three months). Therefore, the alkylene carbonate dilution can be produced and stored in a large amount. In addition, since the alkylene carbonate dilution is in the form of liquid, a desired amount of cyclic mercapto compound can be recovered in a simple manner.

The aqueous reducing chemical agent according to the present invention may be prepared through mixing the alkylene carbonate dilution with an aqueous base material.

The aqueous base material may be water, or a mixture of water and another component such as a surfactant (cationic, anionic, non-ionic, or amphoteric), a water-soluble polymer, a protein hydrolyzate liquid, an organic solvent, an acid, an alkali, a salt, a polyhydric alcohol, a higher alcohol, an ester, a silicone, an oil, a dye, a pigment, or a perfume.

The aqueous base material may further contain a reducing substance such as thioglycolic acid or a salt thereof, cysteine, acetylcystein, cysteamine, thiolactic acid, or thioglycerin, or may contain no such reducing substances. For example, the aqueous base material may be a known No. 1 permanent waving agent containing no reducing substance, or a known No. 1 permanent waving agent itself.

The aqueous reducing chemical agent is, for example, a No. 1 permanent waving agent, a hair-straightening agent, a hair-curling agent, or a straightening permanent agent.

In the preparation of the aqueous reducing chemical agent, the alkylene carbonate dilution according to the present invention may be used, for example, in an amount of 3 to 35 parts by weight per 100 parts by weight of the aqueous base material. When the amount of alkylene carbonate dilution is excessively small, the amount of MBL contained in the dilution decreases, whereas when the amount of alkylene carbonate dilution is excessively large, the amount of alkylene carbonate contained in the dilution becomes excessive. In both cases, waving efficiency may decrease.

The aqueous reducing chemical agent according to the present invention may be prepared simply through uniformly mixing an alkylene carbonate dilution and an aqueous base material. Uniform mixing may be performed simply and rapidly through manually shaking the mixture. Thus, a hair artist can reconstitute the chemical agent upon use in a simple manner for a short period of time. In addition, even when the alkylene carbonate dilution contains a cyclic mercapto compound at high concentration, an aqueous reducing chemical agent solution can be prepared in a very simple manner for a short period of time.

The form of the aqueous reducing chemical agent according to the present invention is generally uniform liquid; i.e., solution. However, the form is not limited to solution, and the chemical agent may be in the form of emulsion, viscous liquid, cream, gel, etc.

The aqueous reducing chemical agent according to the present invention realizes excellent waving efficiency. When the chemical agent is employed as a 2 wt. % (as reduced to thioglycolic acid) No. 1 permanent waving agent, a waving efficiency of 34 to 45% is generally attained, whereas a conventional aqueous MBL solution attains a waving efficiency of 34%. Furthermore, when hair is subjected to permanent waving treatment with the aqueous reducing chemical agent according to the present invention, uniform waving can be realized, and the appearance of waved hair (such as appearance of ridges) are remarkably excellent.

EXAMPLES

The present invention will next be described in detail by way of examples.

<Preparation of Diluted Solutions (Dilutions)>

Examples 1 to 6 and Comparative Examples 1 to 4

MBL was gradually added to each of the diluents given in Table 1, while the mixture was stirred by means of a conventional stirring apparatus, to thereby prepare a diluted solution (dilution) (each of Examples 1 to 6 and Comparative Examples 1 to 4). The mixture was heated at 50° C. or lower in accordance with need. The amounts of MBL and diluents employed are shown in Table 1.

MBL was prepared in accordance with the procedure disclosed in Japanese Patent Application Laid-Open (kokai) No. 2006-199692, specifically through the following procedure. Firstly, 70% sodium hydrosulfide (49 g, 0.6 mmol; product of Junsei Chemical Co., Ltd.) was dissolved in a mixture of methyl alcohol (500 g; product of Junsei Chemical Co., Ltd., special grade) and purified (distilled and ion-exchanged) water (500 g), and the solution was cooled under stirring with ice to 10° C. or lower. To the cooled solution, 2-bromo-4-butyrolactone (100 g, 0.6 mol; product of Tokyo Kasei Kogyo Co., Ltd.) was added dropwise over about 30 minutes. After completion of addition, the liquid was stirred for 10 minutes and, subsequently, concentrated under reduced pressure to about half the volume. The concentrated liquid was extracted with ethyl acetate (500 mL; product of Junsei Chemical Co., Ltd., special grade), and the aqueous layer was further extracted with ethyl acetate (500 mL). The organic phases obtained through extraction were combined and concentrated under reduced pressure, followed by purification through distillation, to thereby produce 23 g of 2-mercapto-4-butyrolactone (b.p.: 94° C./0.3 kpa, yield: 32%).

TABLE 1

| Composition of dilution (wt. %) | | Examples | | | | | | Comparative Examples | | | |
|---|---|---|---|---|---|---|---|---|---|---|---|
| | | 1 | 2 | 3 | 4 | 5 | 6 | 1 | 2 | 3 | 4 |
| Diluent | MBL | 7.7 | 9.1 | 27.5 | 27.5 | 50.0 | 75.0 | 27.5 | 27.5 | 27.5 | 6.7 |
| | Ethylene carbonate | bal. | bal. | bal. | — | bal. | bal. | — | — | — | bal. |
| | Propylene carbonate | — | — | — | bal. | — | — | — | — | — | — |
| | Ethanol | — | — | — | — | — | — | bal. | — | — | — |
| | Benzyl alcohol | — | — | — | — | — | — | — | bal. | — | — |
| | N-Methyl-pyrrolidone | — | — | — | — | — | — | — | — | bal. | — |

<Storage Stability Test of Dilutions>

A dilution of Example 3 was placed in glass vessels, and each vessel was closed with a cap. The samples were stored at 0° C., 5° C., room temperature, 40° C., and 50° C., for three months. After storage, the amount of MBL remaining in each dilution was determined through HPLC. The results (percent MBL remaining) are shown in Table 2.

TABLE 2

| | Storage temp. (° C.) | | | | |
|---|---|---|---|---|---|
| | 0 | 5 | room temp. | 40 | 50 |
| Percent remaining (%) | 97 | about 100 | 97 | 97 | 96 |

<Preparation of 2.5 wt. % MBL-Containing Aqueous Reducing Chemical Agents>

Preparation Examples 1 to 6 and Comparative Preparation Examples 1, 3, and 4

Each of dilutions (Examples 1 to 6 and Comparative Examples 1, 3, and 4) was added to purified water, while the mixture was stirred by means of a stirring apparatus (a stirring apparatus B-100, product of Tokyo Rika Kikai, turbine impeller: 120 rpm), to thereby prepare a 2.5 wt. % MBL-containing aqueous reducing chemical agent solution (each of Preparation Examples 1 to 6 and Comparative Preparation Examples 1, 3, and 4). The amounts of components are shown in Table 3.

Comparative Preparation Example 2

Uniform mixing was performed in a manner similar to that of Preparation Example 1. However, the resultant mixture was separated into two phases; i.e., an aqueous phase and an oil phase (benzyl alcohol phase). Thus, a uniform aqueous reducing chemical agent was failed to be prepared.

Comparative Preparation Example 5

The procedure of preparation Example 1 was repeated, except that non-diluted MBL was added instead of the MBL dilution, and purified water containing POE (20EO) cetyl ether was used instead of purified water itself, to thereby prepare a 2.5 wt. % MBL-containing aqueous reducing chemical agent solution (Comparative Preparation Example 5).

Control

The procedure of preparation Example 1 was repeated, except that non-diluted MBL was added instead of the MBL dilution, to thereby prepare a 2.5 wt. % MBL-containing aqueous reducing chemical agent solution (control).

<Checking of Operability in Preparation of Aqueous Reducing Chemical Agents>

In the preparation of aqueous reducing chemical agents (Preparation Examples 1 to 6, Comparative Preparation Examples 1 to 5, and control), when an MBL dilution or MBL was added to an aqueous medium under stirring, the time required for forming aqueous solution (dissolution time) was measured. Operability in the preparation procedure was evaluated by dissolution time. The results (dissolution time (s) values) are shown in Table 3.

<Waving Efficiency Test>

Each of the aqueous reducing chemical agents (Preparation Examples 1 to 6, Comparative Preparation Examples 1 and 3 to 5, and control) was employed as a No. 1 permanent waving agent, and a 4 wt. % aqueous Na brominate solution was employed as a No. 2 permanent waving agent.

Waving efficiency of each chemical agent was determined through the Kirby method. Specifically, a test hair piece (a tress of hair, length: about 10 cm) was fixed on a Kirby test apparatus. Firstly, the test piece was treated with each of the No. 1 agents at 30° C. for 10 minutes, and rinsed off with flowing water for one minute. Subsequently, the test piece was treated with the No. 2 agent at 30° C. for 10 minutes, and rinsed off with flowing water for one minute. After completion of the two treatment steps, the treated hair piece was removed from the Kirby test apparatus and dried. The dimensions of the thus-obtained dried hair piece were measured, and waving efficiency was calculated in accordance with the following equation:

Waving efficiency (%)=100−[100×($B-A$)]/($C-A$), wherein

A denotes the interval (mm) between the first rod and the sixth rod of the Kirby test apparatus (measured length between the center axis of each rod);

B denotes the length (mm) of a curled hair piece corresponding to six ridges; and C denotes the length (mm) of the curled hair piece corresponding to six ridges as measured after the hair piece has been straightened. The obtained waving efficiency values are in Table 3.

<Evaluation of Wave Appearance>

Waving feature of the hair pieces which had been treated with the permanent waving process were visually evaluated. Table 3 shows the results. The appearance was evaluated on the basis of the following ratings:

DD: appearance of waves was inferior to that of the control hair piece;

CC: appearance of waves was almost equivalent to that of the control hair piece;

BB: appearance of waves was more superior to that of the control hair piece; and AA: appearance of waves was remarkably more superior to that of the control hair piece.

TABLE 3

| Composition of aqueous reducing agent (wt. %) | Preparation Examples | | | | | |
|---|---|---|---|---|---|---|
| | 1 | 2 | 3 | 4 | 5 | 6 |
| Dilution | Ex. 1 32.5 | Ex. 2 27.5 | Ex. 3 9.1 | Ex. 4 9.1 | Ex. 5 5 | Ex. 6 3.3 |
| MBL | — | — | — | — | — | — |
| POP(20EO) cetyl ether | — | — | — | — | — | — |
| Purified water | bal. | bal. | bal. | bal. | bal. | bal. |
| Evaluation Dissolution time (sec) | 24 | 24 | 27 | 28 | 36 | 43 |
| Waving efficiency (%) | 38.2 | 40.4 | 40.4 | 40.4 | 38.2 | 36.0 |
| Wave appearance | BB | AA | AA | AA | BB | BB |

| Composition of aqueous reducing agent (wt. %) | Comparative Preparation Examples | | | | | Control |
|---|---|---|---|---|---|---|
| | 1 | 2 | 3 | 4 | 5 | |
| Dilution | Comp. Ex. 1 9.1 | Comp. Ex. 2 9.1 | Comp. Ex. 3 9.1 | Comp. Ex. 4 37.5 | — | — |
| MBL | — | — | — | — | 2.5 | 2.5 |
| POP(20EO) cetyl ether | — | — | — | — | 5 | — |
| Purified water | bal. | bal. | bal. | bal. | bal. | bal. |
| Evaluation Dissolution time (sec) | 24 | over 120 | 21 | 19 | 63 | 79 |
| Waving efficiency (%) | 33.7 | — | 31.5 | 31.5 | 32.6 | 33.7 |
| Wave appearance | CC | — | DD | DD | DD | — |

As is clear from Tables 2 and 3, the chemical agents of Examples exhibited excellent characteristics.

The alkylene carbonate dilution of the present invention (Example 3) exhibited a percent MBL decomposition after three month of only 4% or less, indicating that the dilution has high storage stability.

The aqueous reducing chemical agents (Preparation Examples 1 to 6), prepared from the corresponding alkylene carbonate dilutions of the present invention, can be rapidly and uniformly dissolved during preparation thereof, and realize high waving efficiency and provide good waving appearance.

In contrast, the aqueous reducing chemical agent (Comparative Preparation Example 1), prepared from a diluted solution formed by means of ethanol, provides unsatisfactory waving appearance.

The aqueous reducing chemical agent (Comparative Preparation Example 2), prepared from a diluted solution formed by means of benzyl alcohol, cannot provide a uniform solution.

The aqueous reducing chemical agent (Comparative Preparation Example 3), prepared from a diluted solution formed by means of N-methylpyrrolidone, and the aqueous reducing chemical agent (Comparative Preparation Example 4), prepared from a <7 wt. % MBL dilution, provide considerably bad waving appearance.

The aqueous reducing chemical agent (Comparative Preparation Example 5), prepared through adding MBL directly to a surfactant-containing aqueous solution, requires a time for attaining uniform dissolution for preparation thereof twice or longer that of the aqueous reducing chemical agent according to the present invention, and provides considerably bad waving appearance.

The aqueous reducing chemical agent (control), prepared through adding MBL directly to water, requires a time for attaining uniform dissolution for preparation thereof three times or longer than that of the aqueous reducing chemical agent according to the present invention.

What is claimed is:

1. An aqueous reducing chemical agent comprising:
   an alkylene carbonate dilution; and
   an aqueous base material,
   wherein the alkylene carbonate dilution is contained in an amount of 3 to 35 wt. % of the aqueous base material, and
   the alkylene carbonate dilution contains a cyclic mercapto compound in an amount of 7 to 80 wt. % and an alkylene carbonate in an amount of 20 to 93 wt. % wherein the alkylene carbonate is a mixture of ethylene carbonate and propylene carbonate, and the ratio (ethylene carbonate/propylene carbonate) by weight is 90/10 to 50/50.

2. The aqueous reducing chemical agent according to claim 1, which is a No.1 permanent waving agent, a hair-straightening agent, a hair-curling agent, or a straightening permanent agent.

3. The aqueous reducing chemical agent according to claim 1, wherein the cyclic mercapto compound is a 2-mercapto-lactone and/or 2-mercapto-lactam.

4. The aqueous reducing chemical agent according to claim 3, wherein the 2-mercapto-lactone is 2-mercapto-4-butyro-lactone.

5. The aqueous reducing chemical agent according to claim 1, wherein the alkylene carbonate is at least one selected from the group consisting of ethylene carbonate and propylene carbonate.

* * * * *